(12) United States Patent
Wu et al.

(10) Patent No.: US 10,788,421 B2
(45) Date of Patent: Sep. 29, 2020

(54) ELECTRONIC ASSAY APPARATUS, METHOD AND KIT THEREOF

(71) Applicant: TAIDOC TECHNOLOGY CORPORATION, New Taipei (TW)

(72) Inventors: Chia-Chi Wu, New Taipei (TW); Tien-Jung Tsai, New Taipei (TW)

(73) Assignee: TAIDOC TECHNOLOGY CORPORATION, New Taipei (TW)

( * ) Notice: Subject to any disclaimer, the term of this patent is extended or adjusted under 35 U.S.C. 154(b) by 282 days.

(21) Appl. No.: 15/817,247

(22) Filed: Nov. 19, 2017

(65) Prior Publication Data
US 2018/0095035 A1    Apr. 5, 2018

Related U.S. Application Data

(63) Continuation of application No. 14/075,551, filed on Nov. 8, 2013, now abandoned.

(30) Foreign Application Priority Data

Nov. 12, 2012    (TW) .............................. 101142139 A (51) Int. Cl.
| | | |
|---|---|---|
| *G01N 21/47* | (2006.01) | |
| *G01N 21/84* | (2006.01) | |
| *G01N 21/25* | (2006.01) | |
| *G01N 21/00* | (2006.01) | |
| *G01N 21/64* | (2006.01) | |
| *G01N 33/52* | (2006.01) | |
| *G01N 33/53* | (2006.01) | |

(52) U.S. Cl.
CPC ............. *G01N 21/47* (2013.01); *G01N 21/00* (2013.01); *G01N 21/255* (2013.01); *G01N 21/8483* (2013.01); *G01N 33/52* (2013.01); *G01N 33/53* (2013.01)

(58) Field of Classification Search
None
See application file for complete search history.

(56) References Cited

U.S. PATENT DOCUMENTS

2005/0196875 A1*    9/2005  Blatt .................... G01N 33/558
                                                                   436/514

* cited by examiner

*Primary Examiner* — Neil N Turk
(74) *Attorney, Agent, or Firm* — Chun-Ming Shih (57) ABSTRACT

The present invention related to an electronic assay apparatus and a testing method thereof. The electronic assay apparatus for determining a result of an assay performed using a test strip comprises three light sources, only one detector and a microprocessor. The three light sources respectively illuminate light incident upon three different zones of the test strip. The detector detects light from the three zones alternately and the distances between the only one detector and the three light sources respectively are almost the same. Further, multiple openings corresponding to the three light sources respectively have the same size and/or shape. The microprocessor compares a calculating result value to only one threshold for showing a result.

18 Claims, 6 Drawing Sheets

ELECTRONIC ASSAY APPARATUS, METHOD AND KIT THEREOF

BACKGROUND OF THE INVENTION

Field of the Invention

The present invention relates to an electronic assay apparatus, a testing method, and a kit thereof for quickly and easily reading assay result.

Description of the Related Art

Lateral flow test strips are known in the art and may be used in clinical diagnosis to determine the presence of an interested analyte in a sample, such as bodily fluid. For example, a lateral flow test strip suitable for the measurement of the pregnancy hormone human chorinic gonadotropin (hCG) is widely commercially available. The test strip usually has a control zone for determining the work of the assay and has a testing zone for determining the present of the interested analyte. However, such widely commercially available strips require the result to be interpreted by the user. Sometimes the result will be erroneous due to a degree of subjectivity, for example, different people may obtain different test results especially when a single color test zone is light and blur, which is undesirable.

Electronic assay apparatuses for reading the result of the test strips are known, according to the matters disclosed in U.S. Pat. No. 7,239,394. A conventional electronic assay apparatus includes a test strip and a circuit broad. The test strip is positioned related to the circuit broad and has a control zone and a test zone. The circuit broad includes a microprocessor, three light sources disposed thereon and two light detectors correspondingly disposed beneath the first light source and the third light source, respectively. The control zone and the test zone are aligned to the first and the third light sources respectively so as to allow the light from the source to illuminate on respectively. The second light source illuminates a reference zone between the control zone and the test zone to obtain a background. The first light detector detects light reflected from the control zone and some of the reference zone and the second light detector detects light reflected from some of the reference zone and the test zone. The microprocessor receives a detection signal from the light detectors for determining response circumstances of the control zone and the test zone. Furthermore, the microprocessor also detects the rate of the change of the reading with respect to time, or d(reading)/d(time) to calculate the result. Alternatively, the rate of change of slope with respect to time may be measured or calculated by $d^2(reading/d)time)^2$. The result is positive when the reading value exceeds an upper threshold and is negative when the reading value lowers a lower threshold.

Furthermore, besides the determination of a single analyte, some tests need to detect over two kinds of analytes at the same time or the determination which can measure the high and the low concentrations of a single analyte simultaneously is designed for improving the sensitivity of the determination. According to the known method disclosed in U.S. Pat. No. 7,879,624 ('624), the determination is implemented on two test strips. The two test strips absorb a sample from the same sample pad, and each test strip has an individual test zone respectively. The cooperative electronic assay apparatus has different light sources to illuminate light upon a test zone, a control zone and a reference zone of each test strip and be received by a detector to obtain a result for avoiding the erroneous judgment from the user. However, said detecting method of using two test strips has some defects. Not only the test zone of each test strip needs to be made respectively during manufacturing but the two test strips should be linked together to the same sample pad. The defects said above may increase the manufacture cost and complicate the process which will also affect the yield rate. Thus, a need exists for improved electronic assay apparatus.

SUMMARY OF THE INVENTION

According to one aspect of the present invention is to provide an electronic assay apparatus that comprises light sources with predetermined positions and detector to achieve results reading.

Furthermore, the present invention provides an electronic assay apparatus for improving the known design of the two test strip detection. The apparatus comprises only one detector and three light sources, and all of them arranged within a fan-shaped region. The detector positioned at the center of circle, and the three light sources positioned anywhere upon the arc of a sector whose circle center is the said detector. By this way, the size of test strips could be smaller and to avoid the erroneous judgment caused by that both the two test strips used the only one control zone and reference zone. Moreover, that could also avoid the possibility of the incomplete flow of the sample due to that both of the two test strips use a single sample pad.

For achieving the objective said above, one skilled method of the present invention is providing an electronic assay apparatus for determining a result of an assay, the apparatus comprises:
  three light sources are aligned for respectively illuminating light incident upon three spatially separated zones of the test strip, wherein the three zones include a test zone, a control zone and a reference zone;
  only one detector to detect light from the three different zones of the test strip and receive the corresponding signals which include a test zone signal, a control zone signal and a reference zone signal, wherein the distances between the only one detector and the three light sources respectively are almost the same; and
  a microprocessor for receiving the signals from the detector and calculating the signals to a result value relating to the test zone signal and the reference zone signal;
  wherein the microprocessor compares the result value to a threshold and generates an output signal, if the result value exceeds the threshold and indicative of a first result, or, alternatively, the output signal indicative of a second result if the result value is less than the threshold.

In a preferred embodiment in accordance with the present invention, the positions of the detector and the three light sources may be designed to arrange within a fan-shaped region. The detector positioned at a center of circle, and the three light sources positioned anywhere upon the arc of a sector whose circle center is the said detector.

In a preferred embodiment in accordance with the present invention, the test strip further includes a second test zone, and the electronic assay apparatus further comprises a fourth light source for illuminating light incident upon the second test zone. Preferably, the second test zone and the test zone are used to detect different analytes or different concentrations of a single analyte.

In a preferred embodiment in accordance with the present invention, the detector and the four light sources could be designed to arrange within a fan-shaped region. The detector positioned at a center of circle and the four light sources positioned anywhere upon the arc of a sector whose circle center is the said detector.

In a preferred embodiment in accordance with the present invention, the apparatus preferred further comprises a baffle which comprises a plurality of shelters defining a plurality of openings corresponding to the light source and the detector respectively. The baffle used to block interferences from outside light source or between the internal light sources. The baffle further comprises a blocker positioned at the suitable site of the detector and is used to block direct light from the light sources. Pluralities of slits are defined between the blocker and the shelters, and for permitting the detector to detect the reflected light from the different zones of the test strip respectively. Multiple openings corresponding to the three light sources respectively may have the same size and/or shape.

The apparatus in accordance with the present invention preferably further comprises an ejective element and a switch. The ejective element used to orientate and eject the test strip. When the ejective element orientates the test strip and then opens the switch, the microprocessor is further activated and turns on the electronic assay apparatus automatically. By this, the user would turn on or off the apparatus automatically through no buttons.

In a preferred embodiment in accordance with the present invention, the baffle further comprises a trigger. The trigger opens the switch when the ejective element orientates the test strip and then makes the test strip to contact the trigger.

Another aspect of the present invention provides an electronic assay apparatus for determining a result of an assay, the apparatus comprises:
three light sources are aligned for respectively illuminating light incident upon the three spatially separated zones of the test strip;
only one detector to detect the reflected light from the three zone of the test strip and obtain the corresponding signals, wherein the detector and the three light sources are arranged within a fan-shaped region, the detector positioned at a center of circle, and the three light sources positioned anywhere upon the arc of a sector whose circle center is the said detector; and
a microprocessor for receiving the signals from the detector and calculating the signals to obtain a result value;
wherein the microprocessor compares the result value to a threshold and generates an output signal, if the result value exceeds the threshold and indicative of a first result, or, alternatively, the output signal indicative of a second result if the result value is less than the threshold.

In a preferred embodiment in accordance with the present invention, the three light sources comprise:
a first light source illuminating light incident upon a test zone of the test strip;
a second light source illuminating light incident upon a control zone spatially separated from the test zone of the test strip;
a third light source illuminating light incident upon a reference zone spatially separated from the test zone of the test strip; and
further comprising a fourth light source illuminating light incident upon a second test zone spatially separated from the test zone of the test strip, wherein the test zone and the second test zone are used to detect different analytes or different concentrations of a single analyte.

Another aspect of the present invention provides an electronic assay apparatus for determining a result of an assay, the apparatus comprises:
three light sources are aligned for respectively illuminating light incident upon the three spatially separated zones of the test strip;
only one detector to detector the reflected light from the three different zones of the test strip and obtain the corresponding signals, wherein the detector and the three light sources are arranged within a fan-shaped region, the detector positioned at a center of circle, and the three light sources positioned anywhere upon the arc of a sector whose circle center is the said detector.

Still another aspect of the present invention provides an electronic assay apparatus for determining the performances of at least one analyte in a sample, the apparatus comprising:
a test strip with a single flow direction and comprising a test zone, a control zone and a reference zone, wherein the test zone for fixing a substance reacting with the analyte and displaying the performance of the analyte;
three light sources are aligned for respectively illuminating light incident upon the test zone, the control zone and the reference zone of the test strip;
only one detector to detect the reflected light from the test zone, the control zone and the reference zone of the test strip and obtain the corresponding signals proportion to the concentration of the analyte, wherein the detector and the three light sources are arranged within a fan-shaped region, the detector positioned at a center of circle, and the three light sources positioned anywhere upon the arc of a sector whose circle center is the said detector; and
a microprocessor for receiving the signals from the detector and calculating the signal to obtain a result value.

Another aspect of the present invention provides a method for testing an assay, which comprises:
positioning a test strip, having a test zone, a control zone and a reference zone, in relation to an electronic assay apparatus, the apparatus comprises a first light source, a second light source, a third light source and only one detector;
receiving an assay sample;
measuring the light level received by the detector;
determining, using a microprocessor and based on the light level, a result of the assay performed on the test strip, and
displaying the result of the assay;
wherein:
the first light source is aligned for illuminating light incident upon the test zone of the test strip;
the second light source is aligned for illuminating light incident upon the control zone of the test strip;
the third light source is aligned for illuminating light incident upon the reference zone of the test strip;
the detector is so positioned as to receive light reflected from the test zone, the control zone and the reference zone alternately, wherein the detector and the first, the second and the third light sources are arranged within a fan-shaped region; the detector positioned at a center of circle, and the three light sources positioned anywhere upon the arc of a sector whose circle center is the said detector; and
the microprocessor compares the result to a threshold and generates an output signal, if the result value exceeds the threshold and indicative of a first value, or, alternatively, the output signal indicative of a second signal if the result value is less than the threshold.

In a preferred embodiment in accordance with the present invention, the result obtained from the microprocessor which compares the light level received from the test zone and the reference zone.

The method in accordance with the present invention preferably further comprises comparing the light level received from the control zone and the reference zone before the result determination, for determining if the test strip works normally.

In a preferred embodiment in accordance with the present invention, the test strip further comprises a second test zone for detecting a different analyte or a different concentration of a single analyte with the test zone, and the electronic assay apparatus further comprises a fourth light source illuminating light incident upon the second test zone.

Another aspect, the present invention provides a pregnancy testing kit comprises the said apparatus and a plurality of test strips.

The word "the same distance" throughout the present invention means the same distance actually or the distance within an acceptable error range of the electronic elements.

The word "light source" throughout the present invention means the device that illuminates visible light, preferably is a LED. The light source is preferably with a more efficiency for working, preferred a green light, a blue light or a yellow-green light.

The word "fan-shaped" throughout the present invention means the range of a sector whose circle center is a detector drawn with any long radius. For example, the fan-shaped can be a semicircle or a sector. The central angle formed by two radii of the sector is less than, equal to or more than 180°.

The word "light level" throughout the present invention means the reflected light or the transmitted light. The reflected light means that the light emitted from the light source and transferred to the detector by the test strip or other liquid, and in this circumstance, the detector and the light source deposited in the same side. The transmitted light means that the light passing through the test strip and usually the detector and the light source deposited in the different sides.

The word "change of electronics" throughout the present invention means any kind of change could be determined by the electronics, for example, the changes of the current, the voltage or the resistivity, etc., preferred is the change of the current or the voltage.

The skilled methods in accordance with the present invention provide simple structure, light sources with lower efficiency for working and a detector, and achieve the objective of accurate result determinations. Furthermore, this could lower the manufacture cost through the simple position disposition of the light sources and the detector and combine simple structure of test strips to obtain accurate results.

The electronic assay apparatus and method in accordance with the present invention has following advantages.

1. The electronic assay apparatus in accordance with the present invention comprises at least three light sources and only one detector, and the simple structure of the apparatus can decrease the manufacturing cost.

2. The electronic assay apparatus in accordance with the present invention is designed to arrange the only one detector and the three light sources within the fan-shaped range; the three light sources preferably positioned anywhere upon the arc of the sector whose circle center is the detector; this may not only decrease structure complexity but decrease the use of the test strips and then decrease the manufacturing cost.

3. The electronic assay apparatus in accordance with the present invention achieve the objective of reading result values through simple light sources and only one detector cooperating with simple algorithms.

4. The operative method of the electronic assay apparatus in accordance with the present invention does not need to additionally detect the flow velocity of the sample so it can decrease processing step to decrease determination complexity and achieve an accurate measurement.

5. The operative method of the electronic assay apparatus in accordance with the present invention compares the result value to only one threshold so the operational process is simple and decreases the calculating complexity.

6. The electronic assay apparatus in accordance with the present invention employs green light, blue light or yellow-green light to detect red color for decreasing noise compared with red light to detect blue color.

7. The pregnancy test kit employed in the present invention comprises one electronic assay apparatus and a plurality of test strip sets for users reusing the electronic assay apparatus conveniently and also saving the costs of users.

8. The electronic assay apparatus in accordance with the present invention is designed with a plurality of shelters and openings, the openings corresponding to the light sources preferably have the same shape and/or size; by this, in the preferred embodiment of the present invention, the light sources does not only have the same distance to the detector but the openings is corresponded with the same shape and/or size, to achieve the objective of precise measurements.

9. In a plurality of light sources of the electronic assay apparatus in accordance with the present invention, the light emitted from each light source upon the detector has the same distance for decreasing the deviation between the light sources and then increasing the accuracy of the measurement.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
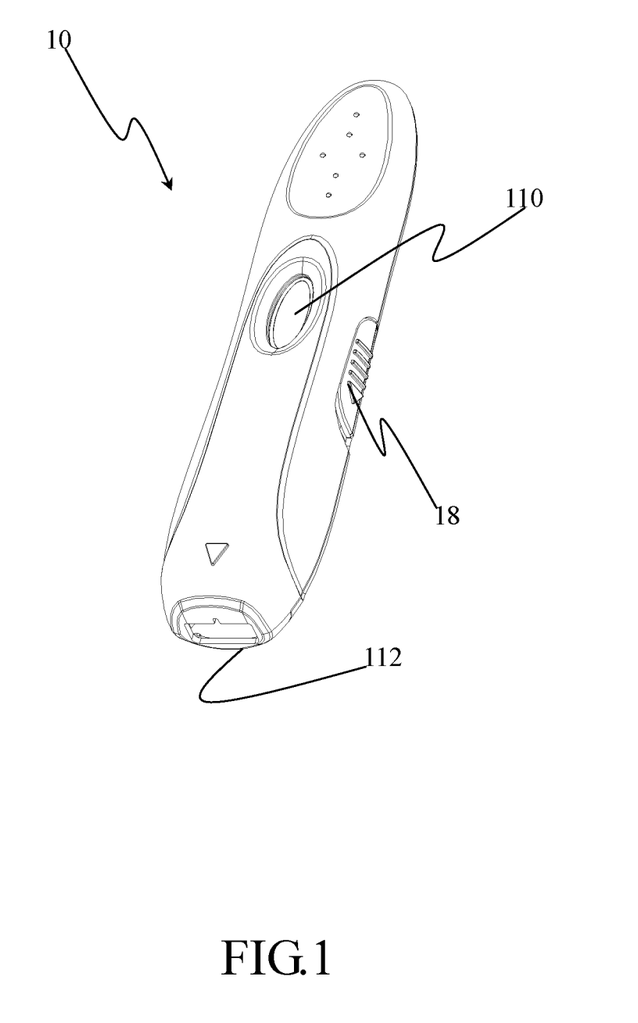
FIG. 1 is a perspective view of an electronic assay apparatus in accordance with the present invention.
Figure 2:
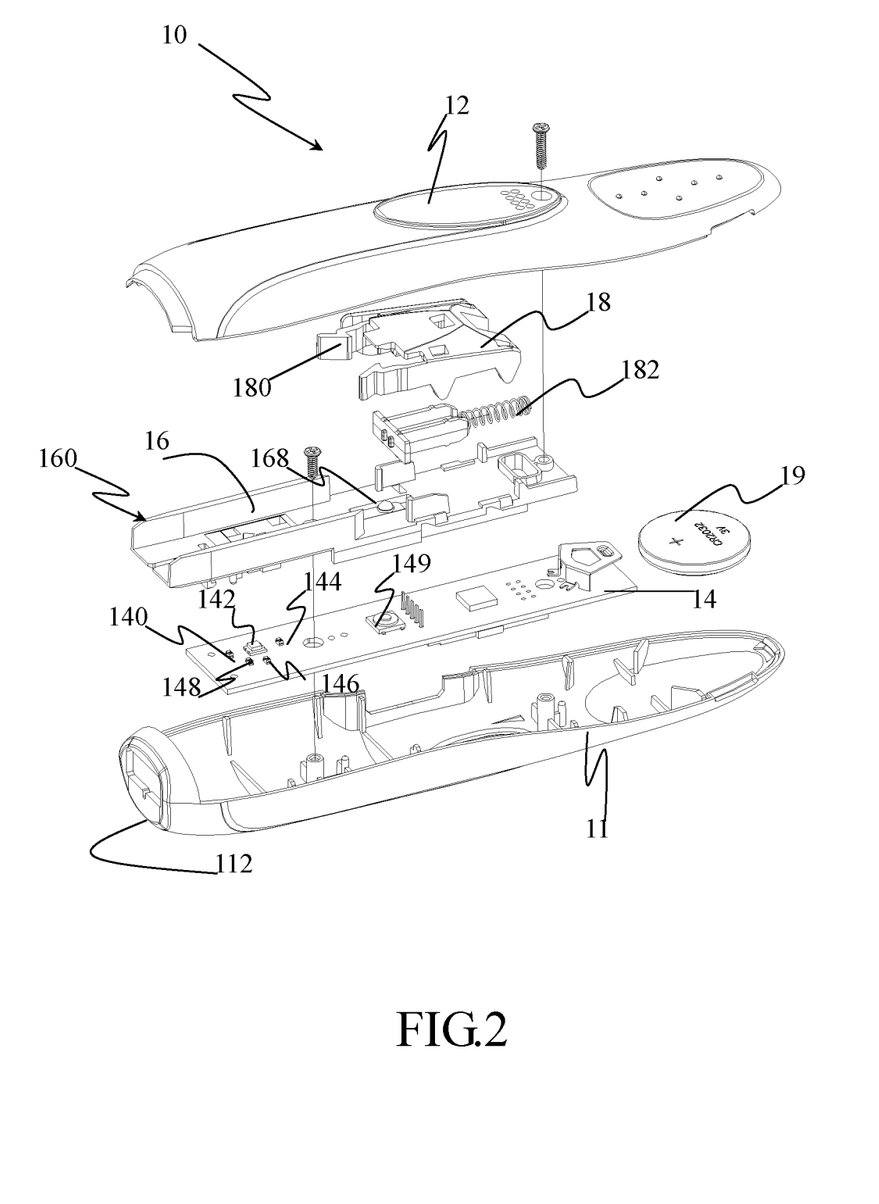
FIG. 2 is a perspective exploded view of the electronic assay apparatus of FIG. 1 in accordance with the present invention.

With reference to FIGS. 1 and 2, they are respectively represent a perspective view and a perspective exploded view of a preferred embodiment of an electronic assay apparatus in accordance with the present invention, the apparatus comprises a cover (10) and a circuit board (14), more preferably, further comprises a baffle (16) and an ejective element (18).

The cover (10) is preferably fabricated by a substance which is light tight and leak less, and designed to allow the least ambient light passing through only. The cover (10) comprises an inserting opening (112) for inserting a test strip set (20). Furthermore, the cover (10) comprises a top cover (11) and a bottom cover (12) connected together to appear the inserting opening (112). The top cover (11) further comprises a display (110) for displaying an assay result through different symbols, numbers, words or patterns, etc., for example, "+", "−", "positive", "negative", "smile face", "cry face", "green" or "red", and so forth. In a pregnancy test, the method of displaying could also be "pregnant" or "not pregnant", etc., and the present invention is not limited to the methods said above.

Figure 4A:
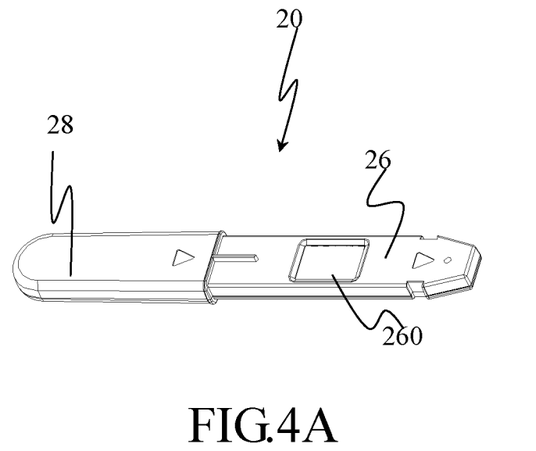
FIG. 4A is a perspective view of a test strip set in accordance with the present invention.
Figure 4B:
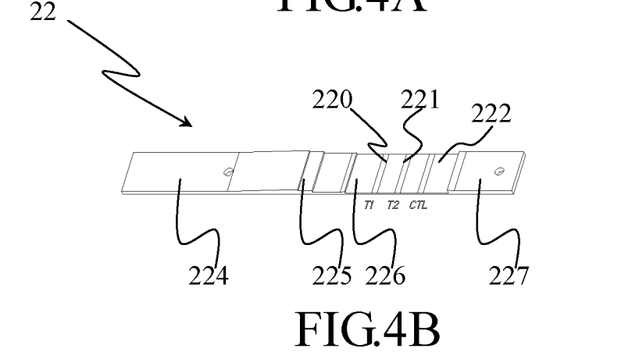
FIG. 4B is a perspective view of certain internal components showing of the test strip set in accordance with the present invention.
Figure 4C:
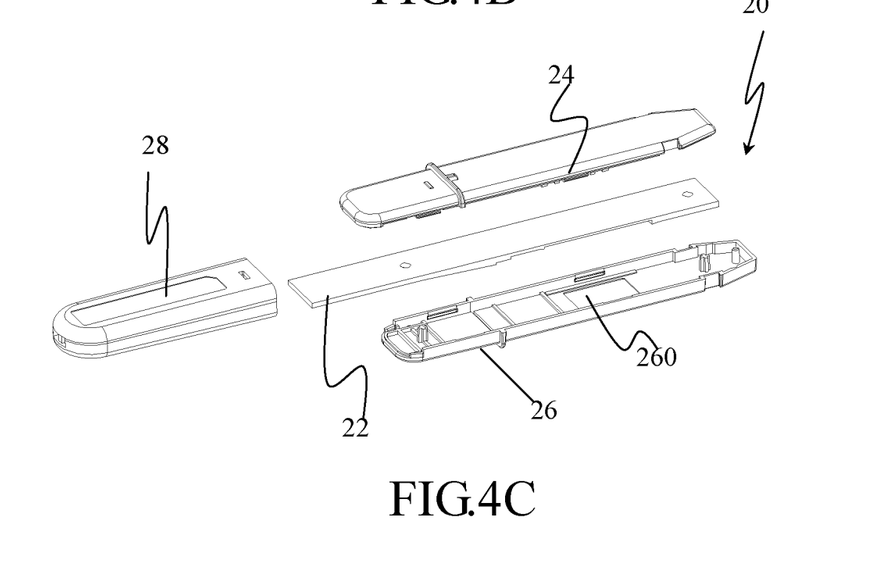
FIG. 4C is a perspective exploded view of the test strip set in accordance with the present invention.

With reference to FIGS. 4A to 4C, a preferred embodiment of a test strip set (20) in accordance of the present invention is used to detect an interested analyte with the electronic assay apparatus. The test strip set (20) is used to detect pregnancy, ovulation, urine and poison test, and so on, and the sample could be urine, sweat, blood, saliva and/or other body fluid. The test strip set (20) comprises a test strip (22) with a housing. The housing comprises a bottom housing (24), a top housing (26) and a lid (28). The bottom housing (24) and the top housing (26) connected together and the lid (28) covers one end of the connected bottom housing (24) and top housing (26) to wrap the test strip (22). The test strip set (20) may not comprise the housing and the present invention is not limited to this. Please referred to FIG. 4B, the test strip (22) comprises a first test zone (220) and a control zone (222) separated a distance to the first test zone (220). The control zone (222) reflects whether the test strip (22) is working normally and the first test zone tests a presence of an interested analyte.

In a preferred embodiment of the present invention, the test strip set (20) further comprises a second test zone (221) which could also be used to detect a presence of an interested analyte. Preferably, the first test zone (220) and the second test zone (221) are used to detect different analytes or different concentrations of an analyte. The test strip (22), moreover, further comprises a reference zone (223) to be used when cooperates with the electronic assay apparatus, the detailed principle and method will be described hereinafter. The arranged method of the first test zone (220), second test zone (221) and control zone (223) is not limited to the illustration of FIG. 4B. The positions of the first test zone and the second test zone could be changed to each other, and the control zone is preferably deposited on the downstream of the sample pad. The top housing (26) further comprises a window (260) for corresponding to and showing the first test zone (220), the second test zone (221) and the reference zone (223).

Figure 5:
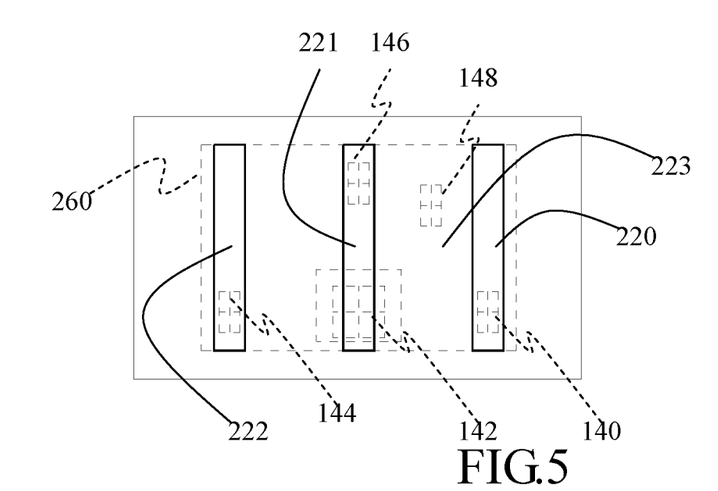
FIG. 5 is an illustration of showing an embodiment of one arrangement of the electronic assay apparatus of FIG. 1 and the certain internal components of the test strip set of the FIG. 2 in accordance with the present invention.
Figure 6:
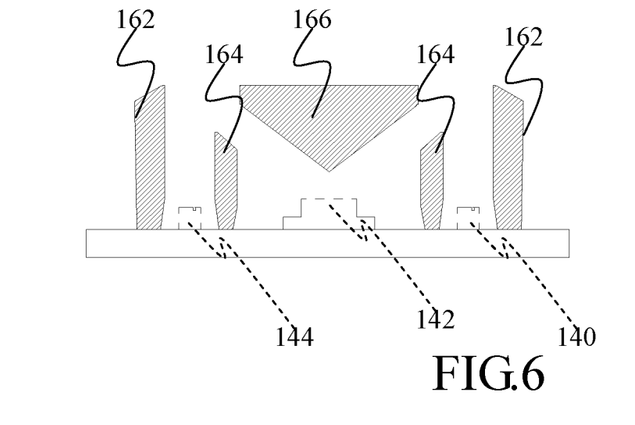
FIGS. 6 to 8 are cross-sectional views with different angle of the corresponding positions between a baffle, light sources and a detector within the electronic assay apparatus of FIG. 1 in accordance with the present invention.
Figure 7:
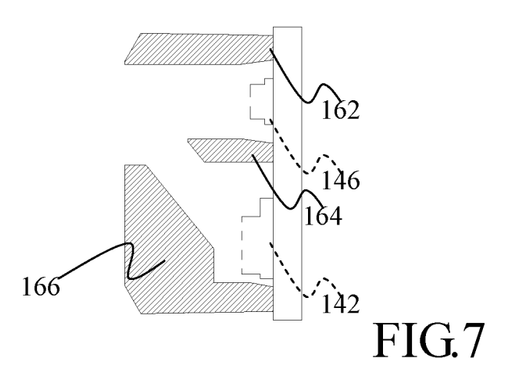
Figure 8:
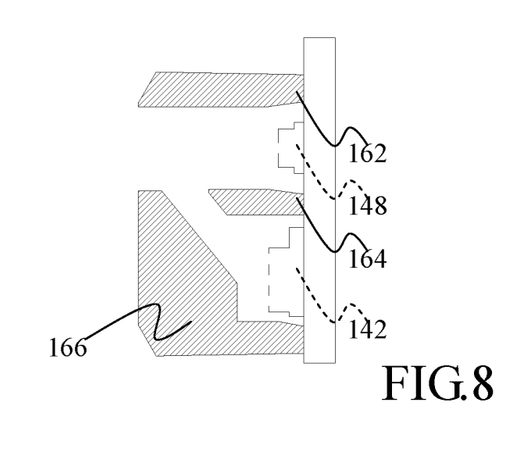

Please referred to FIGS. 2 and 5, the electronic assay apparatus of the present embodiment utilizes to receive the reflected light as an illustration, and the present invention is not limited to this. The circuit board (14) comprises a first light source (140), a detector (142), a second light source (144) and a third light source (146). In a preferred embodiment of the present invention, the circuit board (14) further comprises a fourth light source (148) when the test strip set (20) has a second test zone (221). The first light source (140), the second light source (144), the third light source (146) and the fourth light source (148) deposited on the circuit broad (14) for illuminating light to the first test zone (220), the control zone (222), the reference zone (223) and the second test zone (221) respectively. Preferably, the first light source (140), the second light source (144), the third light source (146) and the fourth light source (148) are capable of emitting a green light, a blue light or a yellow-green light (the wavelength range is 520-580 nm). These light have more efficiency for working.

The detector (142) is deposited between the first light source (140), the second light source (144), the third light source (146) and the fourth light source (148) for detecting the reflected light from the first test zone (220), the second test zone (221), the control zone (222) and the reference zone (223) and transferring signals responsive to the reflected light therefrom. In a preferred embodiment of the present invention, the first light source (140), the second light source (144), the third light source (146) and the fourth light source (148) respectively have the same distance to the detector (142). Preferably, the same distances said above means actually the same or with a deviation within an acceptable range of the electronic elements. Because of the same distance between the light sources and the detector (142), the routes of the light illuminating incident upon the responsive zones emitted from the respective light sources and reflecting to the detector (142) are also the same. The deviation results from the different distances of the emitted light from the light sources received by the detector (142) may be reduced through the aforesaid way. Only one detector (142) may avert correction steps, for example, if a design with two detectors, a deviation is generated between the two detectors, and the reflected or transmitted light detected by the two detectors are unequal and then results in the erroneous determination, so that needs to implement a correction step. The design according to the present invention with only one detector could avert said correction step and reduce the deviation generation.

The detector and the three light sources in accordance with the present invention is designed to be arranged within a fan-shaped region, the detector positioned at a center of circle, and the three light sources positioned anywhere upon the arc of a sector whose circle center is said detector. By this way, the width of the test strip (20) could be decreased, the cost could be reduced, receive the reflected light from the respective zones equally, and reduce the deviation generation to obtain a more accurate result.

The light sources preferred in this embodiment are LEDs, and the detector could also be used to detect transmitted light. The reflected light means that the light emitted from the light source and transferred to the detector by the test strip or other liquids, and in this condition, the detector and the light source deposited in the same side. The transmitted light means that the light passing through the test strip and usually the detector and the light source deposited in the different sides. For achieving the objective of receiving the reflected light, the test strip usually utilizes a layer of white substances with the reflective ability, so that, even if a part of light may pass through the test strip, that may be reflected by the reflective substance.

Further referring to FIG. 5, it is a preferred embodiment of the relative positions between the circuit board and the test strip in accordance with the present invention. The embodiment having two test zones is an example for illustrating, but the present invention is not limited to this. When a test strip (22) is inserted into the apparatus, every light sources (140, 144, 146, 148) are aligned with the respective zones of the test strip (22). The first light source (140) is aligned with the first test zone (220), the second light source (144) is aligned with the control zone (222), the third light source (146) is aligned with the second test zone (221) and the fourth light source (148) is aligned with the reference zone (223). The only one detector (142) detects the light reflected from the four zones and generates the corresponding electronic changes. Preferably, the electronic change may be a current or a voltage, the magnitude of which is proportional to the reflected light detected by the detector (142). The current is converted to a voltage and transferred into an analogue to digital converter (AD) (not shown). The resulting digital signal is received by a microprocessor (not shown).

The microprocessor switches on the light sources (140, 144, 146, 148) one at a time, so that only one of the zones is illuminated at any given time.

Furthermore, the circuit board (14) in accordance with the present invention preferably further comprises a switch (149) electrical connected to the microprocessor. The switch (149) will be closed when the test strip (22) is inserting into the apparatus and controlled by the ejective element (18) described later, and which activates the microprocessor.

Figure 3:
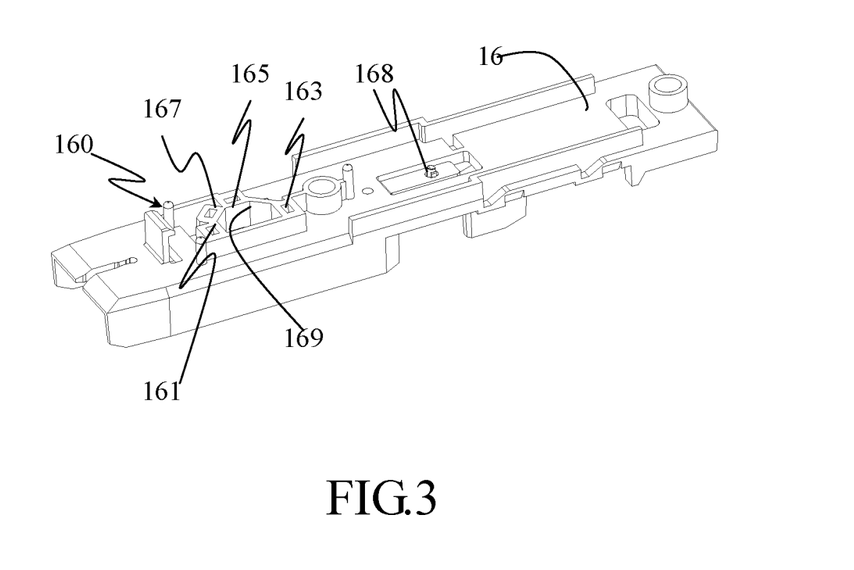
FIG. 3 is a perspective view of a baffle of the electronic assay apparatus in accordance with the present invention.

Please referred to FIG. 3 and FIGS. 6 to 8; FIG. 3 is a preferred embodiment of a baffle at another side of the electronic assay apparatus according to the present invention, the baffle (16) connected with the circuit board (14) and comprises a plurality of shelters (160) defining a plurality of openings (161, 163, 165, 167, 169) corresponding to the light sources (140, 144, 146, 148) and the detector (142) in turn. The plurality of shelters comprise an outer shelter (162) and an inner shelter (164) respectively. The outer shelters are defined respectively corresponding to outside of the light sources (140, 144, 146, 148) and the detector (142) to block light source from outside. The inner shelters corresponding formed inside of the light sources (140, 144, 146, 148) and the detector (142) to avoid the interference between the light sources. In a preferred embodiment according to the present invention, the outer shelter connected with the inner shelter to form enclosures of the plurality of openings (161, 163, 165, 167, 169) respectively. In a preferred embodiment according to the present invention, the openings (161, 163, 165, 167, 169) corresponding to the light sources (140, 144, 146, 148) have the same size and/or shape, the shape may be any suitable shape, more preferably is round or rectangle, but it is not limited to this.

The baffle (16) further comprises a blocker (166) defined upside corresponding to the detector (142) for blocking direct light from the light sources (140, 144, 146, 148), and cooperated with the shelters to define a plurality of slits. The plurality of slits permit the detector (142) to detect the reflected light from the first test zone (220), the second test zone (221), the control zone (222) and the reference zone (223).

The ejective element (18) connected with the baffle (16) posited within the cover (10). In the beginning, the test strip set (20) locks with the ejective element (18) when the test strip set (20) inserts into the apparatus and then the ejective element (18) closes the switch (149) to activate the microprocessor. After the test done, push the ejective element (18) to let the test strip set (20) leave out of the ejective element (18) and then the switch (149) is opened to inactivate the microprocessor and the apparatus will shut down.

Figure 9A:
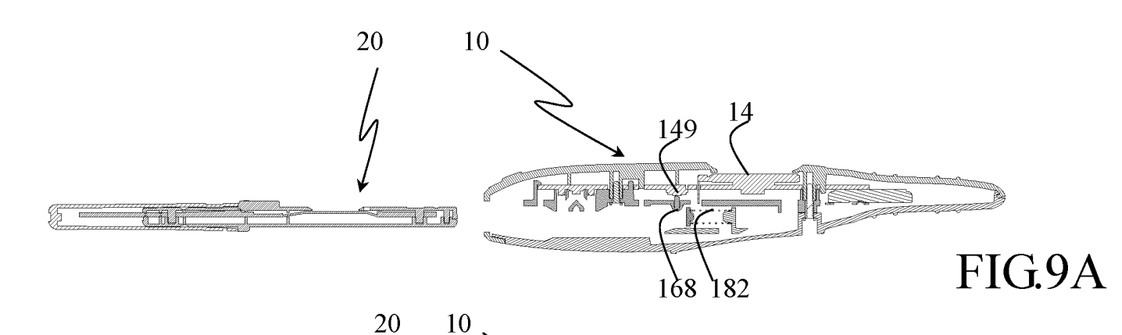
FIGS. 9A to C are preferred flow chart illustrating a method of reading an assay result of the electronic assay apparatus of FIG. 1 in accordance with the present invention.
Figures 9B, 9C:
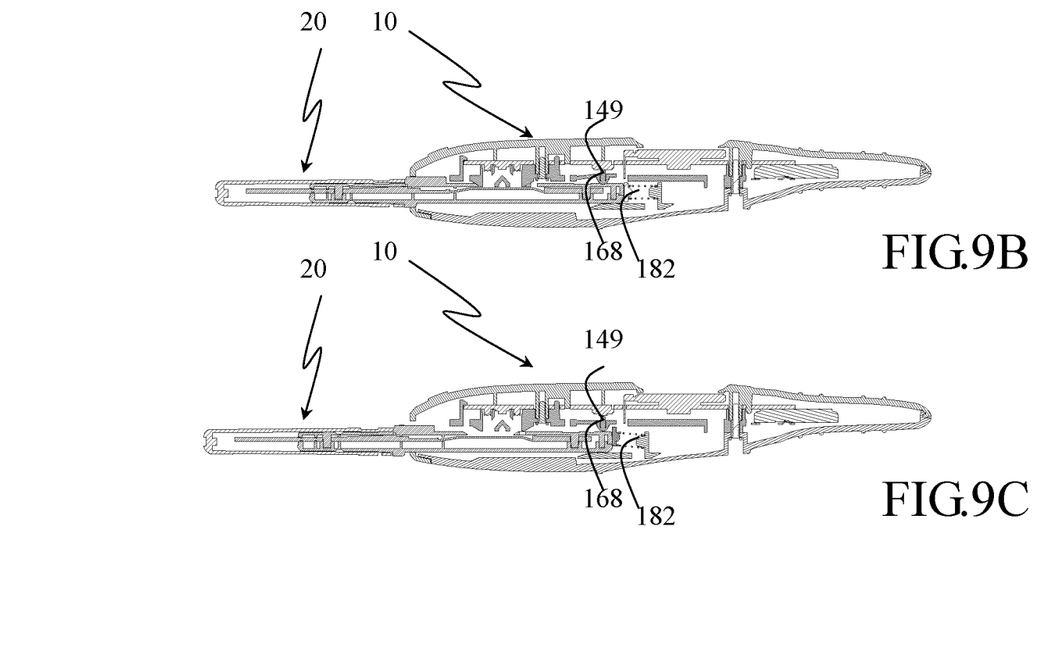

Please referred to FIGS. 9A to C, and reference to FIGS. 2 and 4. These are operation diagrams of the preferred embodiment illustrating the ejective element (18) activating the microprocessor.

The test strip set (20) further comprises a first guiding element (29) (as shown in FIG. 4), and the ejective element (18) further comprises a second guiding element (180). The first guiding element (29) connected with the second guiding element (180) for permitting the test strip set (20) fixed in the apparatus. The methods of the connection of the first guiding element (29) and the second guiding element (180) are not limited, for example, the first guiding element (29) is a notch and the second guiding element (180) is an elastic snap, the elastic snap locks into the notch to fix the test strip set (20) when the test strip set (20) inserts into the apparatus. Further, for example, the first guiding element (29) is a flange and the second guiding element (180) is a concave, the test strip set (20) fixed within the apparatus after the flange connected with the concave. Further, for example, the second guiding element (180) is a sliding groove with a shoulder and the first guiding element is an enlargement, the enlargement may move along the sliding groove and fix at the shoulder.

The ejective element (18) may further comprise an elastic element (182) assembled within the ejective element (18). Before the test strip set (20) inserting into the electronic assay apparatus, the sectional view of the lateral of the apparatus is referred to FIG. 9A. The test strip set (20) compresses the elastic element (182) to lock the first guiding element (29) with the second guiding element (180), and then the test strip set (20) fixed within the apparatus when the test strip set (20) inserts into the electronic assay apparatus (as shown in FIG. 9B), and the test strip set (20) will compress the baffle (16) to contact the switch (149) of the circuit board (14) at this time. In a preferred embodiment according to the present invention, the baffle (16) further comprises a trigger (168), the test strip set (20) compresses the trigger (168) of the baffle (16) to permit the trigger (168) contacting the switch (149). Preferably, the trigger (168) is an elastic piece with a convex protruded from the both side of the elastic piece, the switch (149) is contacted through compressing the convex.

Pushing the ejective element (18) to disconnect the first guiding element (29) of the test strip set (20) and the second guiding element (180) of the ejective element (18) after the test strip set (20) used, and ejecting the test strip set (20) out of the electronic assay element through the resilience of the elastic element (182) as shown in FIG. 9C.

In a further preferred embodiment, the electronic assay apparatus in accordance with the present invention further comprises a power source (19) (as shown in FIG. 2, there is a button cell).

In a preferred embodiment according to the present invention, here utilizing a single test zone as an example for illustrating and the present invention is not limited to this.

The test strip (22) is employed for pregnancy testing and comprises a sample pad (224), a conjugated pad (225), a reaction membrane (226) and an absorbent pad (227) (as shown in FIG. 4B). The conjugated pad (225) comprises mobilized mAb (mouse antibody) anti-Beta hCG conjugated with colloidal gold. The first test zone (220) and the control zone (222) are disposed within the reaction membrane (226). The test zone (220) comprises a vertical line of an antibody to hCG, preferably is an immobilized goat anti-Alpha hCG, and the control zone (222) comprises immobilized goat anti Mouse IgG When a sample is received from the sample pad (224), it will pass through the conjugated pad (225) to bring the mobilized mAb anti-Beta hCG conjugated with colloidal gold, and then pass through the reaction membrane (226) to reaction. If hCG exists in the sample, hCG combined with the mAb anti-Beta hCG conjugated with colloidal gold and combined with the immobilized goat anti-Alpha hCG to form a sandwich Ag-Ab complex and display the red color. Whether the sample contains hCG or not, the mobilized mAb anti-Beta hCG will combine with the goat anti Mouse IgG at the control zone (222) to check whether the test is workable.

Since the test strip (22) uses the red colloidal gold, the apparatus should employ a green, blue or yellow-green light source, and therefore, it can decrease the noise signals compared with red light source illuminating blue color on the test strip as conventional used.

The microprocessor receives the reflected light signals from the test zone, the reference zone and the control zone detected by the detector, and then compares the signals from the test zone and the control zone with the signal from the reference to obtain a first result value and a second result value respectively. Comparing the second result value with a predetermined threshold, when the second result value exceeds the threshold means the test strip works normally. If the second value is less than the threshold means the test strip may have some problems, and it can also display an erroneous signal to warn the users. The first result value is compared to the predetermined threshold; it will show a positive result when the first result value exceeds the predetermined threshold, alternatively, it will indicate a negative result when the said value is less than the predetermined threshold.

According to a preferred embodiment of the present invention, the electronic assay apparatus is for pregnancy testing and the sample is urine. Preferably, the threshold is responsive to samples of urine containing hCG of a concentration of 25 mIU/ml. Since the apparatus according to the present invention detects the reflected light from the test zone, the result value lower than the threshold means the sample contains hCG higher than 25 mIU/ml.

In another preferred embodiment in accordance with the present invention, wherein the test strip has more than two test zones for detecting various items. Such as poison test, the detecting item of the each test zone is selected from the group consisting of Cocaine (COC), Tetrahydrocannabinol (THC), Methamphetamine (MET), Amphetamine (AMP), Ecstasy (MDMA), Morphine (OPI), Phencyclidine (PCP), Benzodiazepines (BZD), Barbiturates (BAR), Methadone (MTD), Tri-cyclic Antidepressants (TCA), Oxycodone (OXY) and the combination thereof.

All of the above items can combine freely, besides MET and AMP. Because of their similar structures, MET and AMP will interfere with each other and they can not be determined at the same test strip.

In the determination, the sample such as urine is absorbed into the test strip from the sample pad and passes through the test zone with various detecting items. The test zone will generate a color when the sample contains the detecting item, and then displaying the result measured by the electronic assay apparatus.

In a preferred embodiment of the present invention, a pregnancy testing and/or ovulation kit is provided. The pregnancy testing and/or ovulation kit comprises one electronic assay apparatus and a plurality of test strip sets for reusing the electronic assay apparatus.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. An assay test kit for determining an analyte within a sample through an assay performed on a test strip, the assay test kit comprising:
    a test strip set comprising the test strip, a housing for holding the test strip and a window positioned on the housing to expose at least three zones of the test strip; and
    an assay apparatus comprising
    a circuit board;
    at least three light sources arranged on the circuit board for respectively illuminating light incident upon the at least three zones of the test strip;
    a detector configured to detect the light from the at least three zones of the test strip and obtain corresponding signals proportional to the analyte, wherein the detector is disposed on a location of the circuit board where the location is corresponding to an inside area of the window;
    a baffle structure connected with the circuit board for holding the test strip, comprising:
        a blocker disposed corresponding to an upside of the detector for blocking direct light from the light sources; and
        a plurality of shelters blocking interferences between the light sources and defining a plurality of openings such that each of the light sources and the detector respectively corresponds to one of the openings, wherein a plurality of slits are defined between the blocker and the shelters for permitting the detector to detect light reflected from the test strip; and
    a microprocessor for receiving the signals from the detector and calculating the signals to a result value;
    wherein routes of light through the plurality of slits defined by the plurality of shelters and the plurality of the openings, respectively emitted from the at least three light sources, respectively incident upon the at least three zones of the test strip and then reflected to the detector are almost the same.

2. The kit as claimed in claim 1, wherein the housing further comprises a bottom housing, a top housing and a lid, the bottom housing and the top housing are connected together, the lid covers one end of the connected bottom housing and the top housing so as to wrap the test strip, and the top housing includes the window.

3. The kit as claimed in claim 1, wherein the at least three zones of the test strip include a first test zone, a control test zone and a reference zone, and the first test zone comprises a first immobilized substance that is configured to react with a first analyte, and the at least three light sources include a first light source for illuminating light incident upon the first test zone, a second light source for illuminating light incident upon the control zone, and a third light source for illuminating light incident upon the reference zone.

4. The kit as claimed in claim 3, wherein the test strip further includes a second test zone spatially separated with the at least three zones of the test strip, the second test zone comprises a second immobilized substance that is configured to react with a second analyte, the assay apparatus further includes a fourth light source for illuminating light incident upon the second test zone, and the second analyte is the same as or different from the first analyte.

5. The kit as claimed in claim 1, wherein the assay test kit is used for pregnancy and/or ovulation testing.

6. The kit as claimed in claim 1, wherein the test strip comprises a sample pad for receiving the sample, a conjugated pad comprising a mobilized substance conjugated with colloidal gold, a reaction membrane and an absorbent pad, the at least three zones of the test strip are arranged on the reaction membrane.

7. The kit as claimed in claim 6, wherein the at least three light sources are configured for illuminating green, blue or yellow-green light.

8. The kit as claimed in claim 6, wherein the housing comprises a bottom housing and a top housing that are connected together to wrap the test strip, and at least a portion of the sample pad is exposed from the connected bottom housing and the top housing, and a lid configured to cover the exposed portion of the sample pad.

9. The kit as claimed in claim 8, further comprising an ejective element for positioning or ejecting the test strip set, and a switch electrical connected to the microprocessor, wherein the ejective element is configured to locking the test strip set when the test strip set inserted for operatively opening the switch that activates the microprocessor and turns the assay apparatus on.

10. The kit as claimed in claim 9, wherein the baffle further comprises a trigger made by elastic piece configured to be compressed by the test strip set for contacting the switch to be an open state.

11. The kit as claimed in claim 1, wherein distances between the detector and the at least three light sources respectively are almost the same.

12. The kit as claimed in claim 1, wherein the microprocessor is configured to compare the result value to a threshold and generates an output signal, the output signal indicative of a first result is generated if the result value exceeds the threshold, and the output signal indicative of a second result is generated if the result value is less than the threshold.

13. The kit as claimed in claim 1, wherein the microprocessor is configured to switch on one of the at least three light sources at a time so that only one of the at least three zones on the test strip is illuminated at any given time.

14. The kit as claimed in claim 1, further comprising a cover comprising a top cover and a bottom cover connected together to form an inserting opening for inserting the test strip, and the top cover comprising a display.

15. The kit as claimed in claim 3, wherein the test strip further includes a second test zone spatially separated with the at least three zones of the test strip, the second test zone comprises a different concentration of the first immobilized substance from the first test zone to detect the first analyte, the assay apparatus further includes a fourth light source for illuminating light incident upon the second test zone.

16. The kit as claimed in claim 1, wherein the window includes relatively long edges and relatively short edges to define the window.

17. The kit as claimed in claim 16, wherein the detector is located along with a long edge of the window.

18. The kit as claimed in claim 17, wherein the detector is aligned with one of the at least three zones.

* * * * *